(12) United States Patent
Kroot et al.

(10) Patent No.: US 7,820,028 B2
(45) Date of Patent: Oct. 26, 2010

(54) OXIDES OF NITROGEN GAS SENSORS AND METHODS

(75) Inventors: Peter J. M. Kroot, Nuenen (NL); Michael L. Rhodes, Richfield, MN (US)

(73) Assignee: Honeywell International Inc., Morristown, NJ (US)

( * ) Notice: Subject to any disclaimer, the term of this patent is extended or adjusted under 35 U.S.C. 154(b) by 1454 days.

(21) Appl. No.: 11/162,251

(22) Filed: Sep. 2, 2005

(65) Prior Publication Data

US 2007/0051641 A1 Mar. 8, 2007

(51) Int. Cl.
*G01N 27/27* (2006.01)
(52) U.S. Cl. .................. 205/781; 204/426; 204/429; 205/783.5; 205/784; 73/23.31; 73/23.32
(58) Field of Classification Search ......... 204/424–429; 205/783.5–785, 781; 73/23.31–23.32, 23.2
See application file for complete search history.

(56) References Cited

U.S. PATENT DOCUMENTS

| | | | |
|---|---|---|---|
| 3,843,400 A | 10/1974 | Radford et al. | |
| 4,199,425 A | 4/1980 | Sinkevitch | |
| 4,272,329 A | 6/1981 | Hetrick et al. | |
| 4,272,330 A | 6/1981 | Hetrick | |
| 4,272,331 A | 6/1981 | Hetrick | |
| 4,358,950 A | 11/1982 | Chang | |
| 4,545,889 A | 10/1985 | Franx | |
| 4,863,583 A * | 9/1989 | Kurachi et al. | 204/424 |
| 4,927,517 A | 5/1990 | Mizutani et al. | |
| 5,290,405 A | 3/1994 | Joshi et al. | |
| 5,401,372 A | 3/1995 | Liu et al. | |
| 5,736,028 A | 4/1998 | Hjortsberg et al. | |

(Continued)

FOREIGN PATENT DOCUMENTS

DE 19838028 3/2000

(Continued)

OTHER PUBLICATIONS

Szabo et al., "Strategies for total NOx measurement with minimal CO interference utilizing a microporus zeolitic catalytic filter," Sensors and Actuators, B 88, pp. 168-177, 2003.

*Primary Examiner*—Nam X Nguyen
*Assistant Examiner*—Bach T Dinh
(74) *Attorney, Agent, or Firm*—Crompton Seager & Tufte LLC

(57) ABSTRACT

Apparatus and methods for measuring $NO_x$ concentrations are disclosed. One method includes the steps of providing a gas stream having a NO concentration and a $NO_2$ concentration, wherein a sum of the NO concentration and the $NO_2$ concentration is a total $NO_x$ concentration; contacting the gas stream with a first zirconium oxide based oxygen sensor at a first temperature to achieve a first $NO:NO_2$ equilibrium at the first temperature; contacting the gas stream with a second zirconium oxide based oxygen sensor at a second temperature to achieve a second $NO:NO_2$ equilibrium at the second temperature; and determining the total $NO_x$ concentration by measuring a response of the first zirconium oxide based oxygen sensor to achieve the first $NO:NO_2$ equilibrium and a response of the second zirconium oxide based oxygen sensor to achieve the second $NO:NO_2$ equilibrium. The second temperature is different than the first temperature.

7 Claims, 6 Drawing Sheets

U.S. PATENT DOCUMENTS

| | | | |
|---|---|---|---|
| 5,897,759 A | 4/1999 | Kurosawa et al. | |
| 6,019,881 A | 2/2000 | Kurosawa et al. | |
| 6,062,064 A * | 5/2000 | Yoshida et al. | 73/23.2 |
| 6,071,393 A | 6/2000 | Oshima et al. | |
| 6,126,902 A | 10/2000 | Kunimoto et al. | |
| 6,136,170 A * | 10/2000 | Inoue et al. | 204/424 |
| 6,143,165 A | 11/2000 | Kurosawa et al. | |
| 6,238,536 B1 | 5/2001 | Lundgren et al. | |
| 6,287,439 B1 | 9/2001 | Kato et al. | |
| 6,303,011 B1 | 10/2001 | Gao et al. | |
| 6,319,377 B1 | 11/2001 | Hasei et al. | |
| 6,344,134 B1 | 2/2002 | Yamada et al. | |
| 6,419,818 B2 | 7/2002 | Kato et al. | |
| 6,533,911 B1 | 3/2003 | Fujita et al. | |
| 6,551,497 B1 | 4/2003 | Gao et al. | |
| 6,764,591 B1 * | 7/2004 | Dutta et al. | 205/781 |
| 6,773,565 B2 | 8/2004 | Kunimoto et al. | |
| 7,217,355 B2 * | 5/2007 | Nair et al. | 205/781 |
| 7,258,820 B2 | 8/2007 | Elangovan et al. | |
| 7,259,126 B2 | 8/2007 | Gordon et al. | |
| 2002/0017461 A1 | 2/2002 | Kunimoto et al. | |

FOREIGN PATENT DOCUMENTS

| | | |
|---|---|---|
| EP | 0257842 | 3/1988 |

* cited by examiner

OXIDES OF NITROGEN GAS SENSORS AND METHODS

BACKGROUND

The present invention generally relates to gas sensors and methods of determining the concentration of gaseous components, and in some cases, to sensors and methods for determining the concentration of oxides of nitrogen ($NO_x$) in a gaseous atmosphere.

Sensors for determining the oxygen composition of gaseous mixtures, such as engine exhaust, are known to the art. For example, U.S. Pat. Nos. 4,272,329, 4,272,330, and 4,272,331 teach an oxygen sensor including a pump cell and a sensor cell, each having solid zirconia electrolyte and thin platinum electrodes attached thereto. The sensor cell and the pump cell, along with a ceramic tube, form an enclosed volume in which the ambient air establishes equilibrium by means of a leak opening in the ceramic tube. The pump cell is connected, by external circuitry, to an electrical input, while the sensor cell is coupled, by external circuitry, to electrical output measurement and control means.

The oxygen sensor taught by the '329 patent is operated in a steady-state mode whereby voltage is applied to the pump cell to electrochemically pump oxygen from the enclosed volume until a steady-state is reached wherein the rate of oxygen pumped from the volume is in equilibrium with the rate of oxygen diffusing into the volume through the leak hole. At steady-state, the oxygen partial pressure in the enclosed volume is reduced from ambient, causing an EMF to develop across the electrodes of the sensor cell. By adjusting the pump cell current to provide a constant sensor cell voltage, the pump cell current is linearly proportional to the percentage oxygen in the ambient atmosphere.

The oxygen sensor taught by the '330 patent uses a similar device operated in a transient mode to measure oxygen partial pressure. After ambient atmosphere of a desired oxygen partial pressure is established in the enclosed volume, the pump cell is activated to withdraw oxygen from the enclosed space. Reduction of oxygen partial pressure in the enclosed space causes an EMF to develop across the sensor cell. The first derivative of sensor cell voltage/time evaluated at or shortly after the initiation of a voltage drop is inversely proportional to the ambient oxygen partial pressure. The oxygen sensor may also be operated by pumping oxygen into the enclosed space and reversing the sign of the initial sensor cell voltage to determine the ambient oxygen partial pressure.

The oxygen sensor taught by the '331 patent uses a similar device operated in an oscillatory mode whereby a repetitive sequence of oxygen pumping currents flow to the pump cell in response to voltage inputs from the sensor cell. The pump cell withdraws oxygen from the enclosed space until the voltage drop induced at the sensor cell equals a predetermined reference value. The polarity of the pump cell current is then reversed to pump oxygen into the enclosed space until the sensor cell voltage reaches another predetermined reference value, at which time the pump cell current is again reversed and the cycle is repeated. With the magnitude of the pump cell current fixed, the period of oscillation is proportional to the oxygen partial pressure.

Sensors for determining the oxides of nitrogen ($NO_x$) composition of gaseous mixtures, such as engine exhaust, are known to the art. For example, U.S. Pat. No. 6,344,134, discloses a method of measuring $NO_x$ concentration using a two-serial-space $NO_x$ sensor. The sensor includes a first pumping cell and a second pumping cell each comprising a solid electrolyte. In the sensor, a measurement gas space, a first space, and a second space communicate in series with each other. The method includes the steps of: pumping out oxygen from the first space into, for example, the measurement gas space, or pumping oxygen into the first space from, for example, the measurement gas space by action of the first pumping cell so that the oxygen concentration in the vicinity of a gas inlet of the second space becomes such that a portion of NO in the first space dissociates; dissociating residual NO and $O_2$ in gas introduced into the second space from the first space by action of the second pumping cell; pumping out oxygen ions generated by dissociation of NO and $O_2$ from the second space by action of the second pumping cell; and determining the concentration of $NO_x$ in the measurement gas based on signals (for example, pumping currents) issued from the first and second pumping cells.

Existing oxide-based gas sensors do not meet either performance or cost needs to address new environmental regulations, particularly with regard to engine exhaust. Improved oxide-based gas sensors are desired.

SUMMARY

The present disclosure generally relates to gas sensors and methods of determining the concentration of gaseous components, and in some cases, to sensors and methods for determining the concentration of oxides of nitrogen ($NO_x$) in a gaseous atmosphere.

In one illustrative embodiment, a method for measuring gas component concentrations is disclosed. The method includes the steps of providing a gas stream having a NO concentration and a $NO_2$ concentration, wherein a sum of the NO concentration and the $NO_2$ concentration is a total $NO_x$ concentration; contacting the gas stream with a first zirconium oxide based oxygen sensor at a first temperature to achieve a first $NO:NO_2$ equilibrium at the first temperature; contacting the gas stream with a second zirconium oxide based oxygen sensor at a second temperature to achieve a second $NO:NO_2$ equilibrium at the second temperature; and determining the total $NO_x$ concentration by measuring a response of the first zirconium oxide based oxygen sensor to achieve the first $NO:NO_2$ equilibrium and a response of the second zirconium oxide based oxygen sensor to achieve the second $NO:NO_2$ equilibrium. The second temperature is different than the first temperature.

In another embodiment, a method includes the steps of providing a gas stream having a NO concentration and a $NO_2$ concentration at a first $NO:NO_2$ equilibrium at a first temperature, wherein the total of the NO concentration and the $NO_2$ concentration is a total $NO_x$ concentration; contacting the gas stream with a zirconium oxide based oxygen sensor at a second temperature to achieve a second $NO:NO_2$ equilibrium at the second temperature, the second temperature is different than the first temperature; and determining the total $NO_x$ concentration by measuring a response of the zirconium oxide based oxygen sensor to achieve the second $NO:NO_2$ equilibrium.

In still a further embodiment, $NO_x$ sensor apparatus includes a first zirconium oxide based oxygen sensor in fluid connection with a $NO_x$ gas source and in electrical connection with a sensor controller. The first zirconium oxide based oxygen sensor includes a first platinum sense electrode. A heating element is in thermal communication with the first zirconium oxide based oxygen sensor. A second zirconium oxide based oxygen sensor is in fluid connection with the $NO_x$ gas source and in electrical connection with the sensor controller. The first zirconium oxide based oxygen sensor includes a second platinum sense electrode.

In a further embodiment, an $NO_x$ sensor apparatus includes a porous media including a catalyst that assists in $NO+\frac{1}{2}O_2 \leftrightarrow NO_2$ equilibrium and in fluid communication with a $NO_x$ gas source. A zirconium oxide based oxygen sensor in fluid communication with the porous media and in electrical connection with a sensor controller. The zirconium oxide based oxygen sensor includes a platinum sense electrode and a heating element is in thermal communication with the first zirconium oxide based oxygen sensor.

These and other aspects of the present application will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

The invention may be more completely understood in consideration of the following detailed description of various embodiments of the invention in connection with the accompanying drawings, in which.

Figure 1:
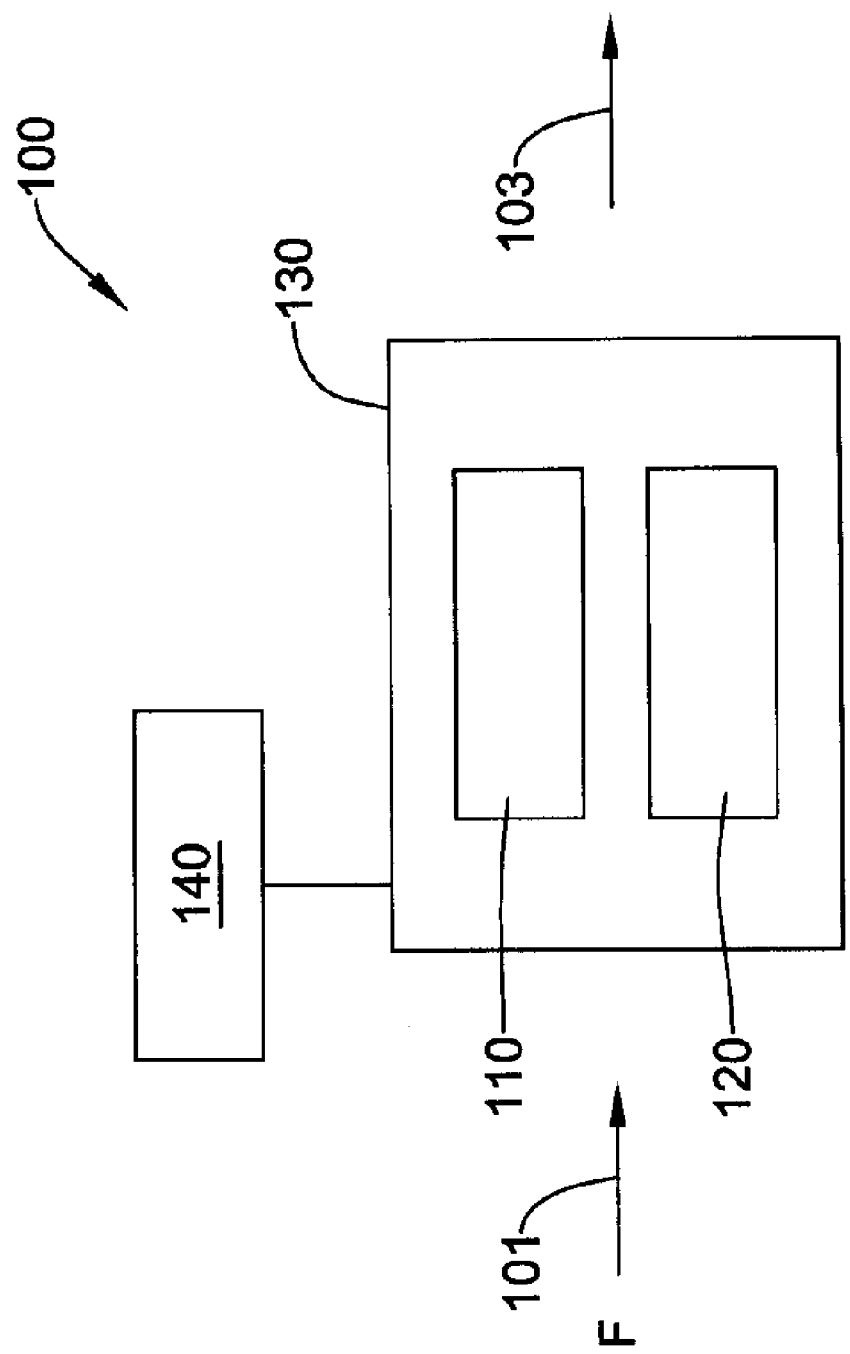
FIG. 1 is a diagrammatic plan view of an illustrative $NO_x$ sensor apparatus.

While the invention is amenable to various modifications and alternative forms, specifics thereof have been shown by way of example in the drawings and will be described in detail. It should be understood, however, that the intention is not to limit the invention to the particular illustrative embodiments described. On the contrary, the intention is to cover all modifications, equivalents, and alternatives falling within the spirit and scope of the invention.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials may be illustrated for the various elements, those skilled in the art will recognize that many of the examples provided have suitable alternatives that may be utilized.

Generally, the present invention pertains to gas sensors and methods of determining the concentration of oxides on nitrogen ($NO_x$) in a gaseous atmosphere. While the present invention is not so limited, an appreciation of various aspects of the invention will be gained through a discussion of the various illustrative embodiments and examples provided below.

Oxides of nitrogen concentrations in a gas are generally governed by the equilibrium:

$NO+\frac{1}{2}O_2 \leftrightarrow NO_2$.

In addition, at equilibrium the ratio of $NO_2$ to NO can be predicted from the equation:

$$(pNO_2)/pNO=1.6\times10^{-4}\cdot\exp(13,900/RT)\cdot(pO_2)^{1/2}.$$

For example, at 750 degrees centigrade and 1% excess oxygen, the equilibrium ratio is 0.01503 (i.e., 98.5% NO and 1.5% $NO_2$. Thus, at any specified temperature and known oxygen concentration, at equilibrium the ratio of $NO_2$ to NO can be predicted.

The oxygen sensors described herein provide a response to gas samples that have an initial non-equilibrium ratio of $NO_2$ to NO at the sensor temperature to monitor the approach toward the equilibrium ratio of $NO_2$ to NO at the sensor temperature. In some embodiments, the sensor apparatus uses two zirconium oxide based oxygen sensors or alternatively one zirconium oxide based oxygen sensor and a catalytic porous membrane, all maintained at known temperatures, to monitor the approach toward the equilibrium ratio of $NO_2$ to NO at the individual sensor temperature. By maintaining the elements at different temperatures, different equilibriums are approached without need to know the gas source initial conditions. Competing reactions such as from, for example, carbon monoxide and methane, proceed to completion and do not interfere with the determination of total $NO_x$.

FIG. 1 is a diagrammatic plan view of an illustrative $NO_x$ sensor apparatus 100. The sensor 100 includes a first zirconium oxide based oxygen sensor 110 (described below) in fluid connection with a $NO_x$ gas source F and in electrical connection with a sensor controller 140. A second zirconium oxide based oxygen sensor 120 is in fluid connection with the $NO_x$ gas source F and is also in electrical connection with the sensor controller 140. In many embodiments, the sensor apparatus 100 includes a housing 130 disposed about the first zirconium oxide based oxygen sensor 110 and the second zirconium oxide based oxygen sensor 120. In some embodiments, a porous media including a catalyst that assists in $NO+\frac{1}{2}O_2 \leftrightarrow NO_2$ equilibrium is in fluid communication with a $NO_x$ gas source F and disposed between the gas source F and the first zirconium oxide based oxygen sensor 130 or the second zirconium oxide based oxygen sensor 140.

In operation, the illustrative $NO_x$ sensor apparatus 100 functions by providing a gas stream 101 having a NO concentration and a $NO_2$ concentration and contacting the gas stream 101 with the first zirconium oxide based oxygen sensor 110 at a first temperature to achieve a first $NO:NO_2$ equilibrium at the first temperature, and contacting the gas stream 101 with a second zirconium oxide based oxygen sensor 120 at a second temperature to achieve a second $NO:NO_2$ equilibrium at the second temperature. The second temperature is different than the first temperature. The sum of the NO concentration and the $NO_2$ concentration is a total $NO_x$ concentration. Total $NO_x$ concentration is determined by measuring the response of the first zirconium oxide based oxygen sensor 110 to achieve the first $NO:NO_2$ equilibrium and the response of the second zirconium oxide based oxygen sensor 120 to achieve the second $NO:NO_2$ equilibrium. In many embodiments, the gas stream 101 includes oxygen at an oxygen concentration. An exiting gas stream 103 is shown flowing away from the first and second zirconium oxide based oxygen sensors 110, 120.

In many embodiments, the first zirconium oxide based sensor 110 and/or the second zirconium oxide based sensor 110 includes a catalyst that assists in providing the gas stream having a specified $NO:NO_2$ equilibrium ($NO+\frac{1}{2}O_2 \leftrightarrow NO_2$) at each specified temperature. The catalyst can be any useful catalyst as described below.

Figure 5:
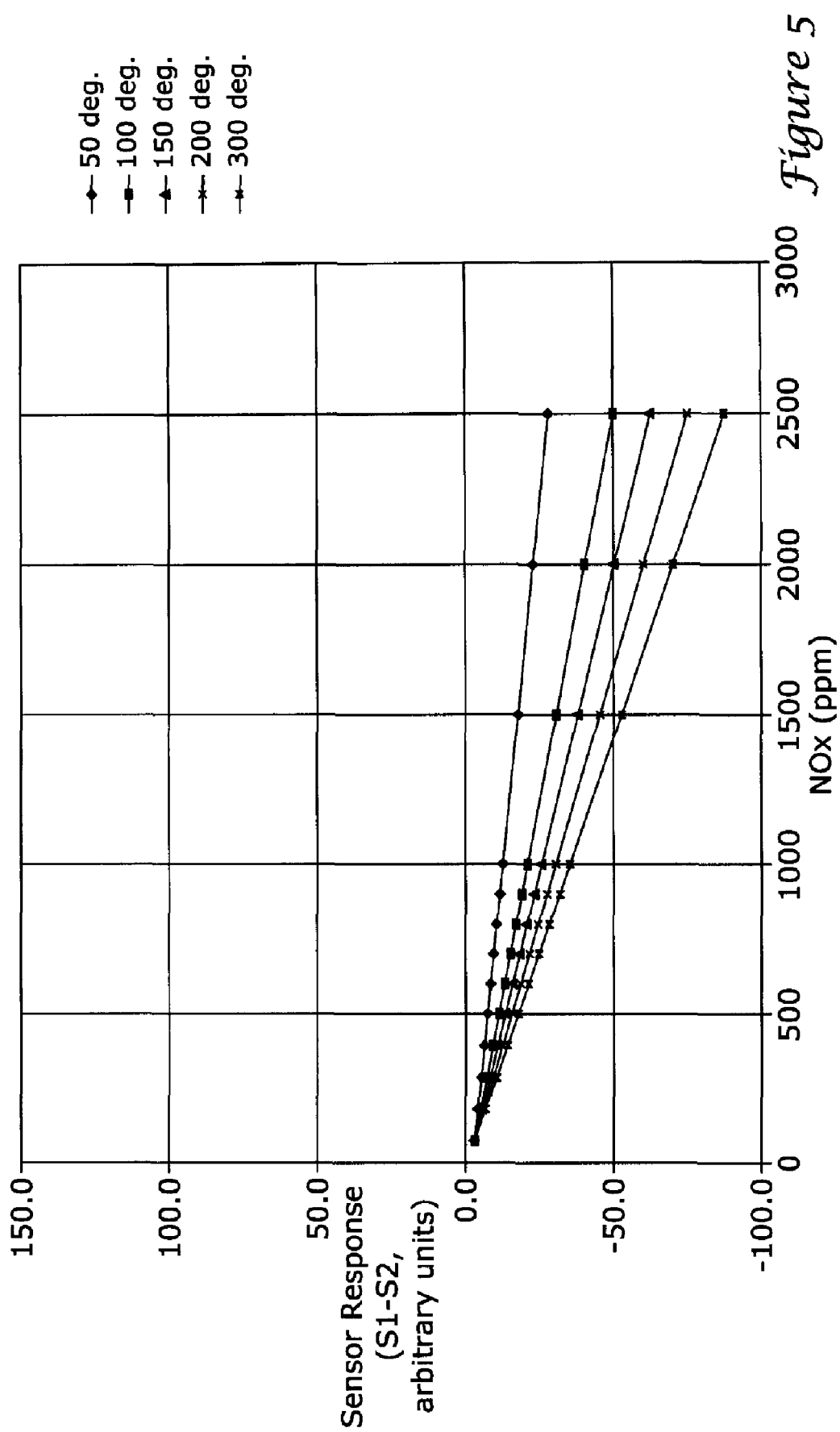
FIG. 5 is an illustrative graph of sensor response verses concentration of $NO_x$ for the sensor apparatus shown in FIG. 1.

In some embodiments, total $NO_x$ concentration is determined by measuring a difference of the response of the first zirconium oxide based oxygen sensor 110 to achieve the first $NO:NO_2$ equilibrium and the response of the second zirconium oxide based oxygen sensor 120 to achieve the second $NO:NO_2$ equilibrium. FIG. 5 is an illustrative graph of sensor response verses concentration of $NO_x$ for the sensor apparatus 100 shown in FIG. 1.

Figure 2:
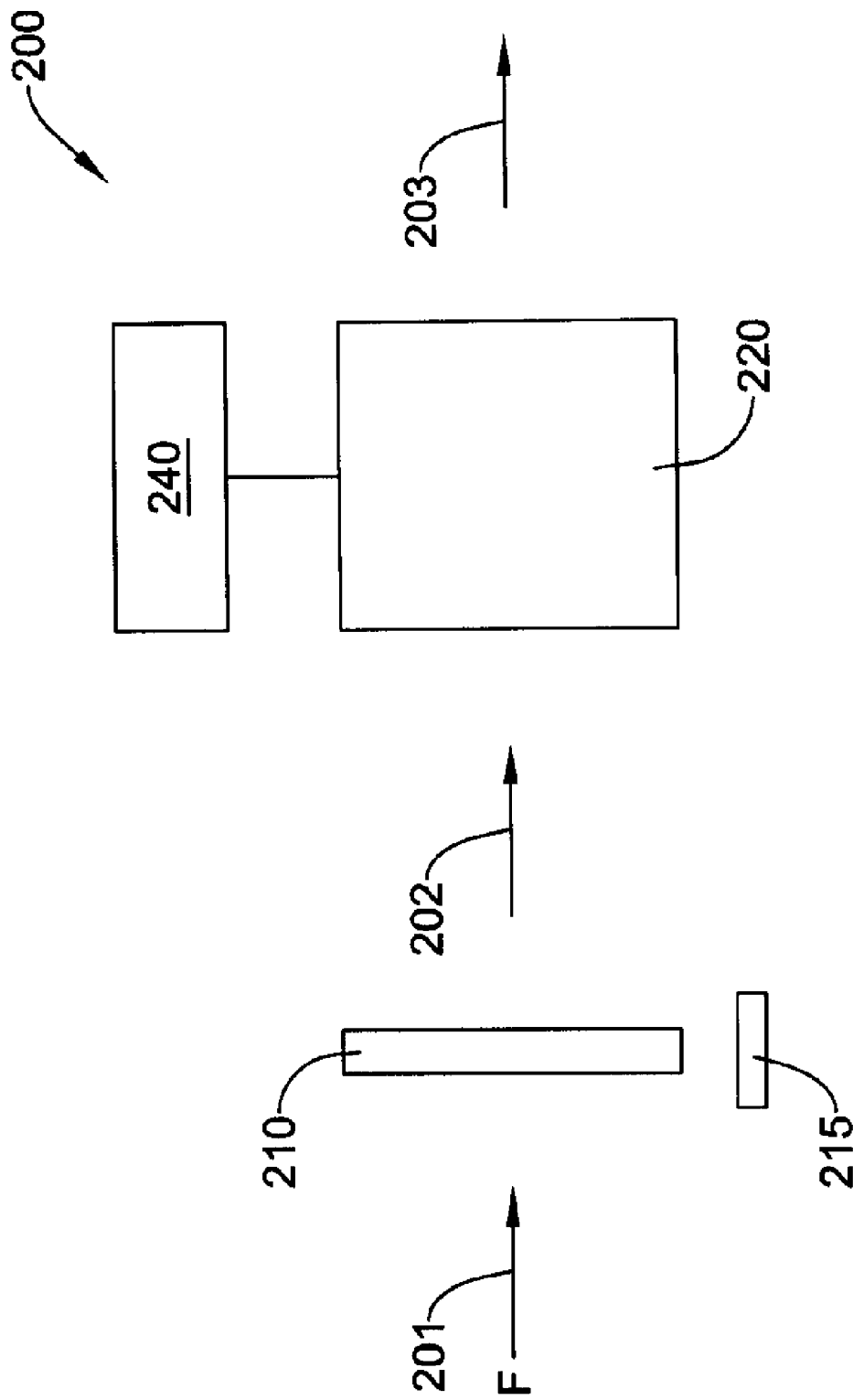
FIG. 2 is a diagrammatic plan view of another illustrative $NO_x$ sensor apparatus.

FIG. 2 is a diagrammatic plan view of another illustrative $NO_x$ sensor apparatus 200. The sensor apparatus 200 includes a porous media 210 that includes a catalyst that assists in $NO+\frac{1}{2}O_2 \leftrightarrow NO_2$ equilibrium and in fluid communication with a $NO_x$ gas source F. The catalyst can be any useful catalyst as described below. A zirconium oxide based oxygen sensor 220 (described below) is in fluid communication with the porous media 210 and in electrical connection with a sensor controller 240. An optional heating element 215 is shown thermal communication with the porous media 210.

In operation, the illustrative $NO_x$ sensor apparatus 200 functions by providing a gas stream 202 having a NO concentration and a $NO_2$ concentration at a first $NO:NO_2$ equilibrium at a first temperature and contacting the gas stream 202 with a zirconium oxide based oxygen sensor 220 at a second temperature to achieve a second $NO:NO_2$ equilibrium at the second temperature. The second temperature is different than the first temperature. The sum of the NO concentration and the $NO_2$ concentration is a total $NO_x$ concentration. The total $NO_x$ concentration can be determined by measuring a response of the zirconium oxide based oxygen sensor 220 to achieve the second $NO:NO_2$ equilibrium. An exiting gas stream 203 is shown flowing away from the zirconium oxide based oxygen sensor 220.

Figure 6:
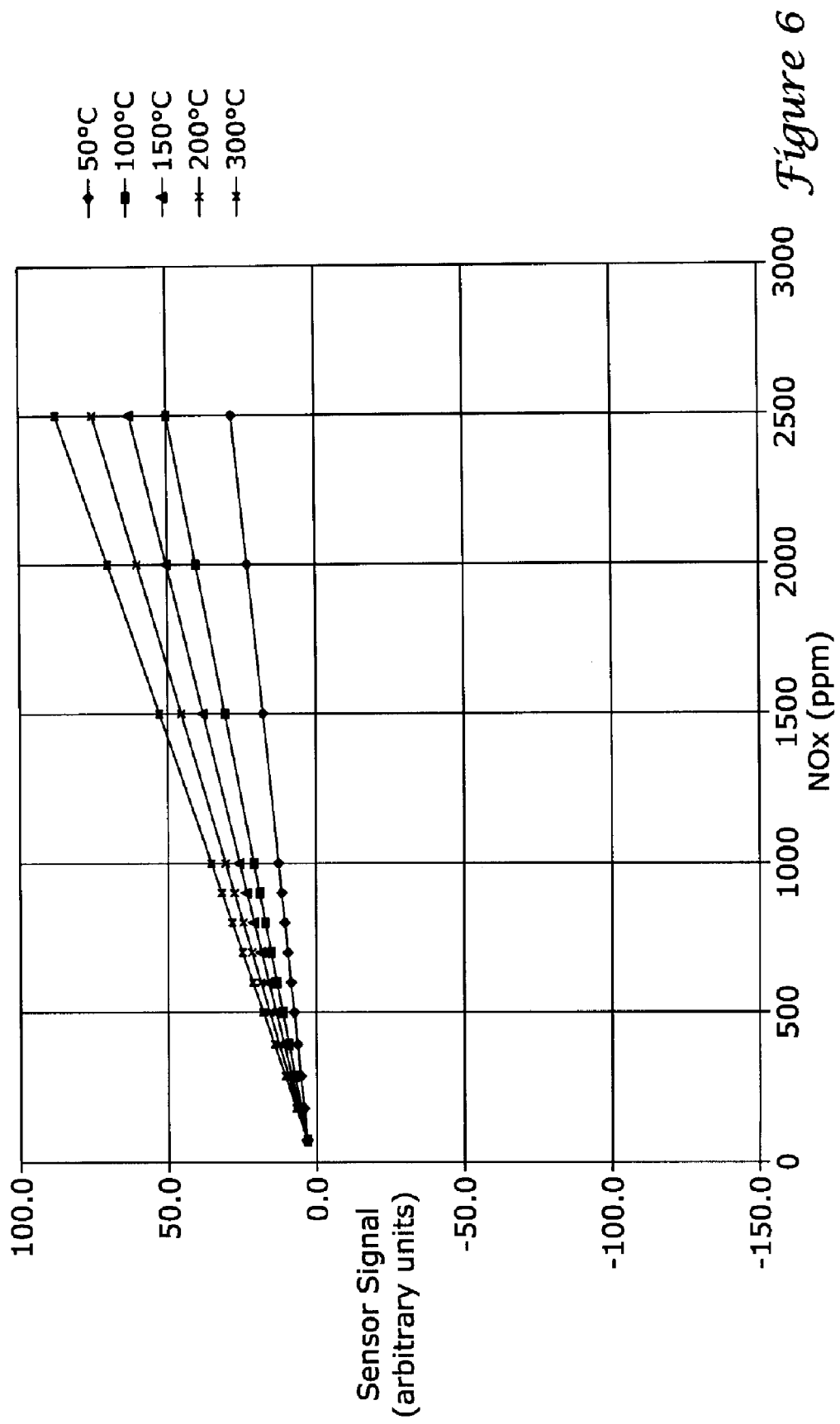
FIG. 6 is an illustrative graph of sensor response verses concentration of $NO_x$ for the sensor apparatus shown in FIG. 2.

In many embodiments, the gas stream 202 is provided by flowing source gas 201 through a porous media 210 including a catalyst, at a first temperature, that assists in providing the first $NO:NO_2$ equilibrium at the first temperature. The catalyst can be any useful catalyst as described below. In many embodiments, the gas stream 202 includes oxygen at an oxygen concentration. FIG. 6 is an illustrative graph of sensor response verses concentration of $NO_x$ for the sensor apparatus 200 shown in FIG. 2.

Figure 3:
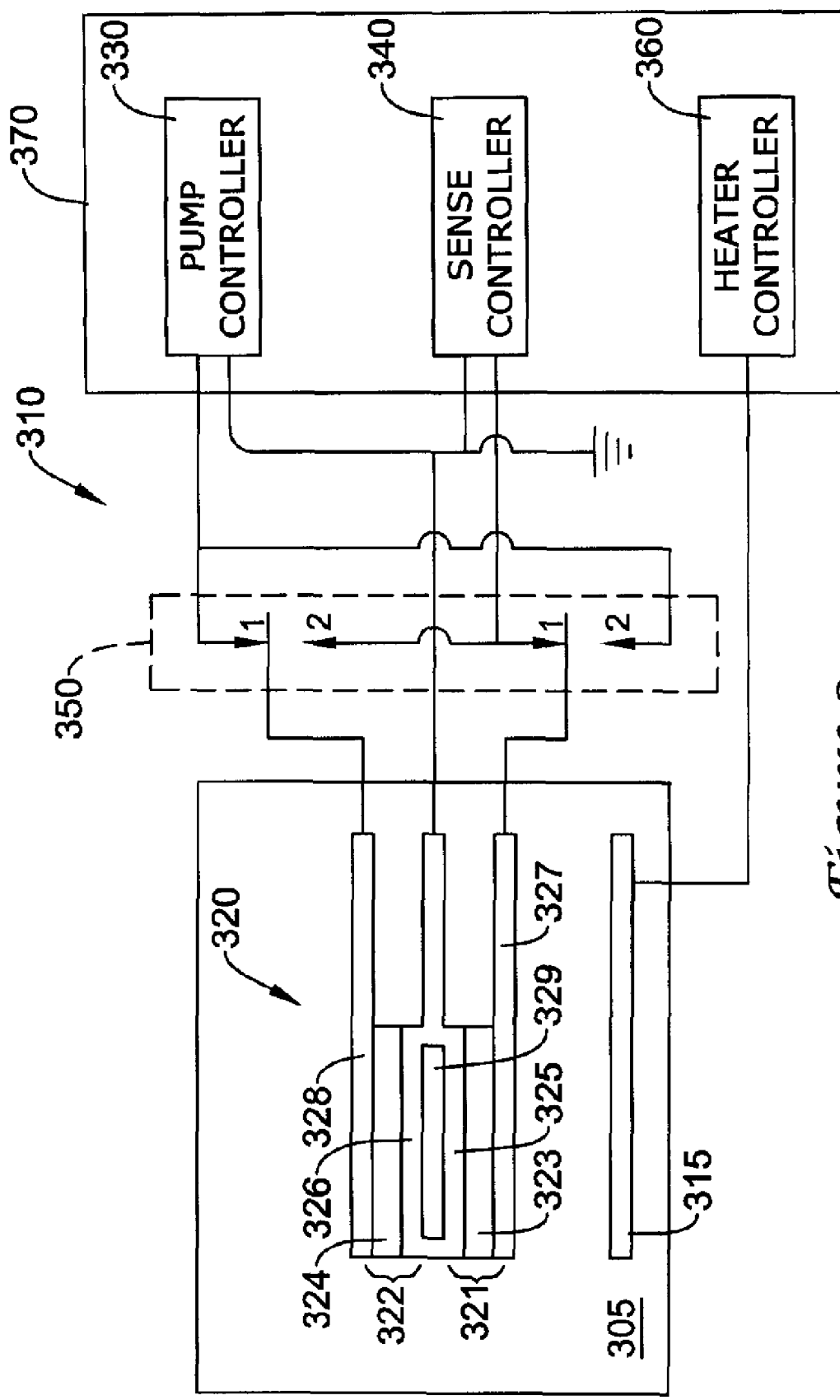
FIG. 3 is a schematic cross-sectional view of an illustrative zirconium oxide based oxygen sensor device in a first position.

FIG. 3 is a schematic cross-sectional view of an illustrative zirconium oxide based oxygen sensor 310 in a first position 1. The gas sensor 310 includes a sensor element 320 electrically coupled to a pump controller 330 and a sense controller 340. As used herein, the term "controller" refers to electronics and/or software. The sensor element 320 is disposed within a first space 305 in fluid communication with a gas source containing one or more gases to be measured by the sensor element 320, such as, for example oxygen and oxides of nitrogen. In many embodiments, the gases to be measured are NO and $NO_2$ or $NO_x$ respectively, where $NO_x=NO+NO_2$. An optional heating element 315 is shown electrically coupled to a heater controller 360 and in thermal communication with the sensor 310. The heating element 315 can modify a temperature at which the sensor element 320 senses at. In the illustrative embodiment shown, the pump controller 330, sense controller 340, and the heater controller 360 are disposed within a controller module 370, but this is not required. The sensor element 320 includes a first cell 321 and a second cell 322. The sensor element 320 can be any configuration such as, for example, cylindrical or planar.

The first cell 321 includes an oxygen-ion conductive solid electrolyte layer 323 such as a zirconium oxide layer disposed between two first cell conductive electrodes 325 and 327. In one embodiment, the first cell conductive electrodes 325 and 327 are first cell platinum electrodes 325, 327. In some embodiments, the first cell electrode 327 includes a catalyst 319 that assists in $NO+\frac{1}{2}O_2 \leftrightarrow NO_2$ equilibrium. The catalyst 319 can be any useful catalyst such as, for example, gold, nickel, or rhodium. The catalyst 319 can be a layer of catalyst disposed on an outer surface of the first cell electrode 327. In many embodiments, the catalyst 319 is formed in a layer from 0.1 to 5 micrometers thick and can be applied by any useful deposition technique.

The second cell 322 includes an oxygen-ion conductive solid electrolyte layer 324 such as a zirconium oxide layer disposed between two second cell conductive electrodes 326 and 328. In some embodiments, both of the second cell conductive electrodes 326 and 328 are second cell platinum electrodes 326 and 328. In one embodiment, the first cell 321 and second cell 322 inner electrodes 325 and 326 is a common platinum electrode. A sealed measurement space 329 is disposed within the sensor element 320.

FIG. 3 shows the sensor element 320 electrically coupled to the pump controller 330 and sense controller 340 in a first position 1. In this embodiment, the first cell 321 is electrically coupled to the pump controller 330 and the second cell 322 is electrically coupled to the sense controller 340. In one embodiment, the first cell 321 has a layer of zirconium oxide 323 disposed between the outer electrode 327 and the inner electrode 325; the second cell 322 has a layer of zirconium oxide 324 disposed between the outer electrode 328 and the inner electrode 326. In this configuration, a total $NO_x$ gas concentration can be determined.

Figure 4:
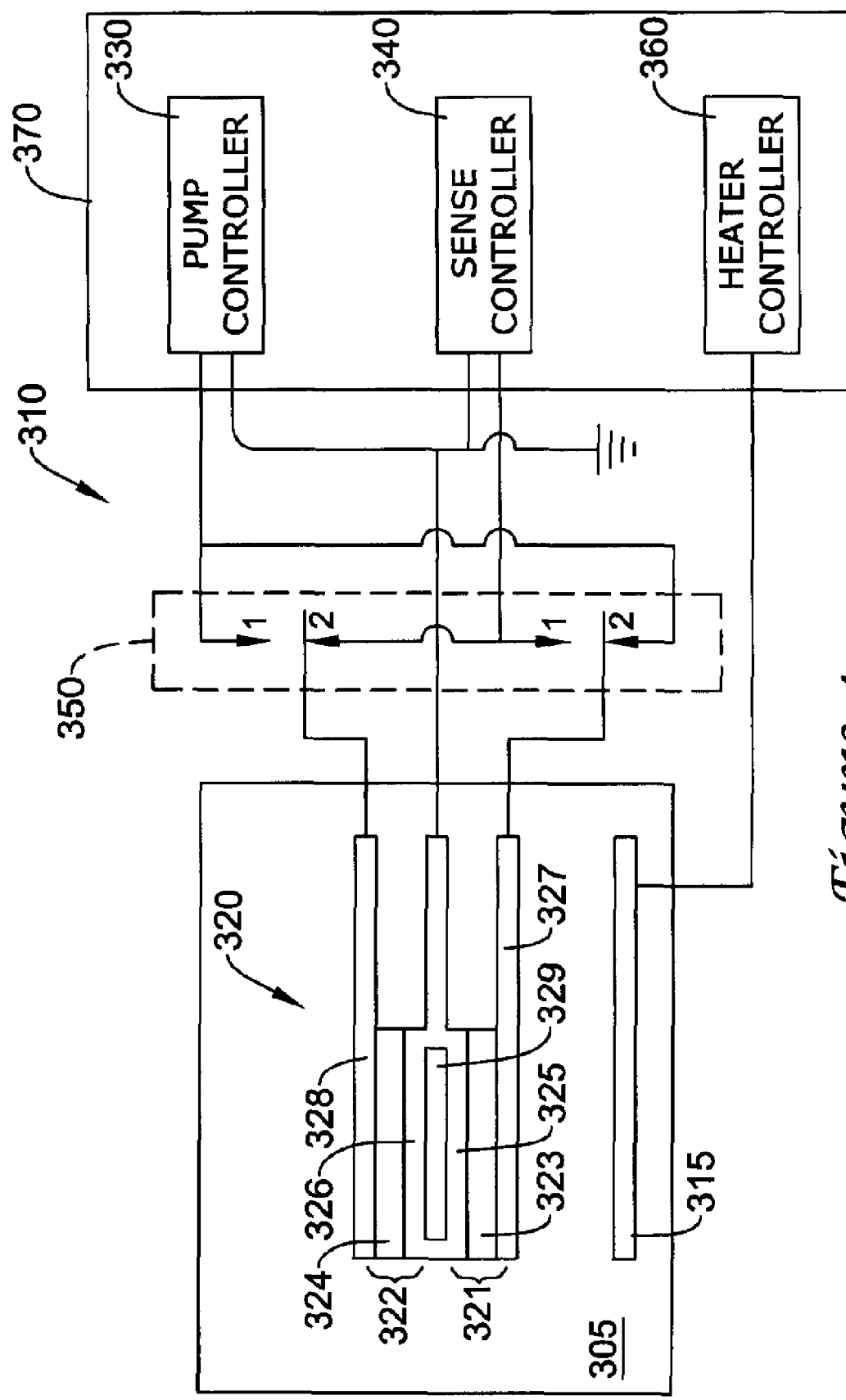
FIG. 4 is a schematic cross-sectional view of an illustrative zirconium oxide based oxygen sensor device in a second position.

In some embodiments, the pump controller 330 and the sense controller 340 can be optionally switched to be electrically coupled to either the first cell 321 or second cell 322 via a switching element 350, as shown in FIG. 4 wherein the sensor element 320 is electrically coupled to pump controller 330 and sense controller 340 in a second position 2. In this configuration, oxygen concentration can be measured.

The switching element 350 can be controlled by hardware and/or software capable of switching the electrical signal routing from the first cell 321 and second cell 322 to the pump controller 330 and the sense controller 340. Pump controllers 330 and sense controllers 340 are well known in the art. When a pump controller 330 is electrically coupled to, for example, the first cell 321, and a pumping current is applied, ion pumping action takes place between the first cell electrodes 325 and 327. Concurrently, the second cell electrodes 326 and 328 cooperate to detect an electromotive force induced therebetween, as is known.

The present invention should not be considered limited to the particular examples described above, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

What is claimed is:

1. A method of calculating a total NOx concentration, comprising steps of:
  providing a gas stream having a NO concentration and a NO2 concentration, wherein a sum of the NO concentration and the NO2 concentration is a total NOx concentration;
  contacting the gas stream with a first zirconium oxide based oxygen sensor at a first temperature to measure a first oxygen concentration and then using the first oxygen concentration to predict a first ratio of NO:NO2 at equilibrium at the first temperature;

contacting the gas stream with a second zirconium oxide based oxygen sensor at a second temperature to measure a second oxygen concentration and then using the second oxygen concentration to predict a second ratio of NO:NO2 at equilibrium at the second temperature, the second temperature being different than the first temperature; and calculating the total NOx concentration using the first ratio of NO:NO2 at equilibrium and the second ratio of NO:NO2 at equilibrium.

2. A method of calculating the total NOx concentration according to claim 1 wherein the providing a gas stream step comprises providing a gas stream further comprising an oxygen concentration.

3. A method of calculating the total NOx concentration according to claim 1 wherein the contacting the gas stream with a first zirconium oxide based sensor step comprises contacting the gas stream with a first zirconium oxide based sensor comprising a catalyst that assists in providing the gas stream having the first ratio of NO:NO2 at equilibrium at the first temperature.

4. A method of calculating the total NOx concentration according to claim 1 wherein the contacting the gas stream with a second zirconium oxide based sensor step comprises contacting the gas stream with a second zirconium oxide based sensor comprising a catalyst that assists in providing the gas stream having the second ratio of NO:NO2 at equilibrium at the second temperature.

5. A method of calculating the total NOx concentration according to claim 1 wherein the contacting the gas stream with a first zirconium oxide based sensor step comprises contacting the gas stream with a first zirconium oxide based sensor comprising a catalyst that assists in providing the gas stream having the first ratio of NO:NO2 at equilibrium at the first temperature and the contacting the gas stream with a second zirconium oxide based sensor step comprises contacting the gas stream with a second zirconium oxide based sensor comprising a catalyst that assists in providing the gas stream having the second ratio of NO:NO2 at equilibrium at the second temperature.

6. A method of calculating the total NOx concentration according to claim 1 wherein the calculating step comprises measuring a difference of the response of the first zirconium oxide based oxygen sensor to achieve the first ratio of NO:NO2 at equilibrium and the response of the second zirconium oxide based oxygen sensor to achieve the second ratio of NO:NO2 at equilibrium.

7. A method according to claim 1 wherein the contacting step comprises contacting the gas stream with a zirconium oxide based oxygen sensor comprising a catalyst that assists in providing the gas stream having a NO concentration and a NO2 concentration at the second ratio of NO:NO2 at equilibrium at the second temperature.

* * * * *